United States Patent [19]

Lewitus

[11] Patent Number: 5,429,120
[45] Date of Patent: Jul. 4, 1995

[54] SUB-SURFACE VISUALIZATION DEVICE

[76] Inventor: Ricardo Lewitus, 65 Lake Shore Dr., Marlboro, Mass. 01752

[21] Appl. No.: 110,529

[22] Filed: Aug. 23, 1993

[51] Int. Cl.⁶ ............................ A61B 1/24; A61C 3/00
[52] U.S. Cl. ............................ 600/191; 433/29; D16/135; 359/803
[58] Field of Search ................ 128/22, 12, 13, 15, 128/16, 23; 433/29, 30, 31; 359/802, 803, 811; D16/135

[56] References Cited

U.S. PATENT DOCUMENTS

| | | | |
|---|---|---|---|
| D. 269,185 | 5/1983 | Tweedie | D16/135 |
| 1,067,572 | 7/1913 | Abbott | 128/12 |
| 1,246,338 | 11/1917 | Smit | 128/16 |
| 1,415,347 | 5/1922 | Heidbrink | 128/12 |
| 2,240,402 | 4/1941 | Joroslow | 359/803 X |
| 2,586,723 | 2/1952 | Sakols | D16/135 X |
| 2,653,597 | 9/1953 | Canan | 128/15 |
| 3,545,433 | 12/1970 | Horn | 128/15 |
| 3,848,587 | 11/1974 | McDonald | 128/9 |
| 4,483,588 | 11/1984 | Dalbo et al. | 350/247 |
| 4,564,355 | 1/1986 | Traiger et al. | 433/215 |
| 4,592,726 | 6/1986 | Brilliant | 433/31 |
| 4,697,578 | 10/1987 | Burgin | 128/16 |
| 4,757,616 | 7/1988 | Hills | 33/488 |
| 4,790,751 | 12/1988 | Reinhardt et al. | 433/29 |
| 5,031,918 | 7/1991 | Brill | D16/135 X |
| 5,055,040 | 10/1991 | Clar | 433/29 X |
| 5,168,405 | 12/1992 | Feinbloom | 359/802 |

FOREIGN PATENT DOCUMENTS 210600  2/1924  United Kingdom ................ 128/13

OTHER PUBLICATIONS

Bausch & Lomb May 1969 Catalog, "Industrial Magnifiers: Principles, Selection, and Use"; p. 13.
"New Mouth Prop," Mushin, William W.; Dec. 1936, p. 525.

Primary Examiner—Richard J. Apley
Assistant Examiner—Donna L. Maraglio

[57] ABSTRACT

The invention relates to a device and method for increasing the visualization of biological tissues and underlying structures. A particular application is to examine gums for pre-emergent teeth. One embodiment has a cylindrical lens portion and an offset handle which may also serve as a port of entry for light sources to brighten the viewing area. The method involves pressing body tissue with the device which serves to vacate the area of blood which increases light transmission through the tissue and enhances contrast between bone/teeth structure and flesh.

1 Claim, 5 Drawing Sheets

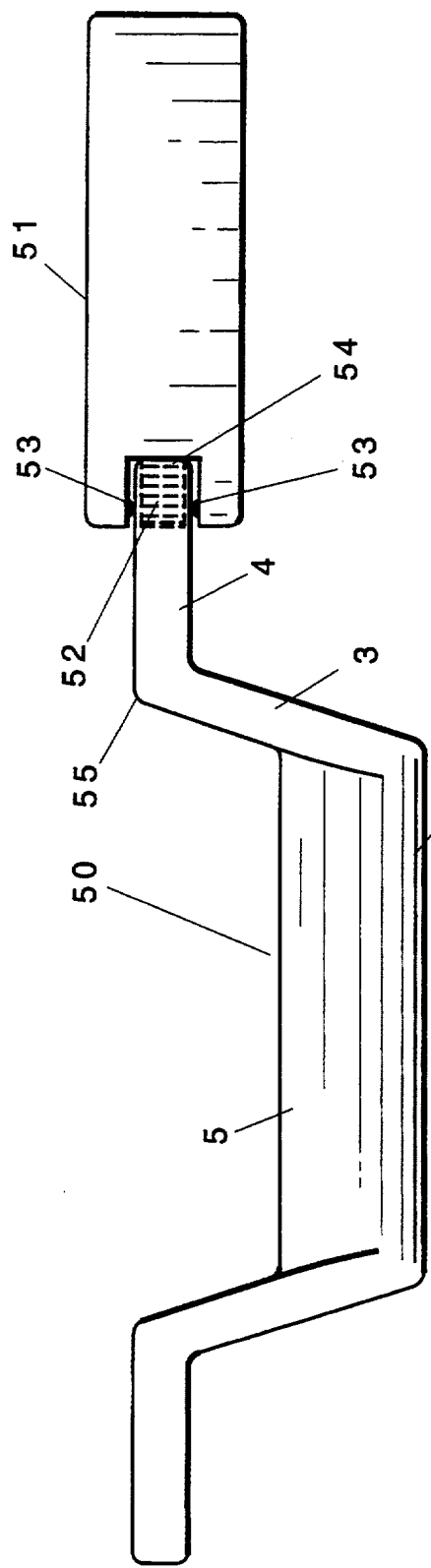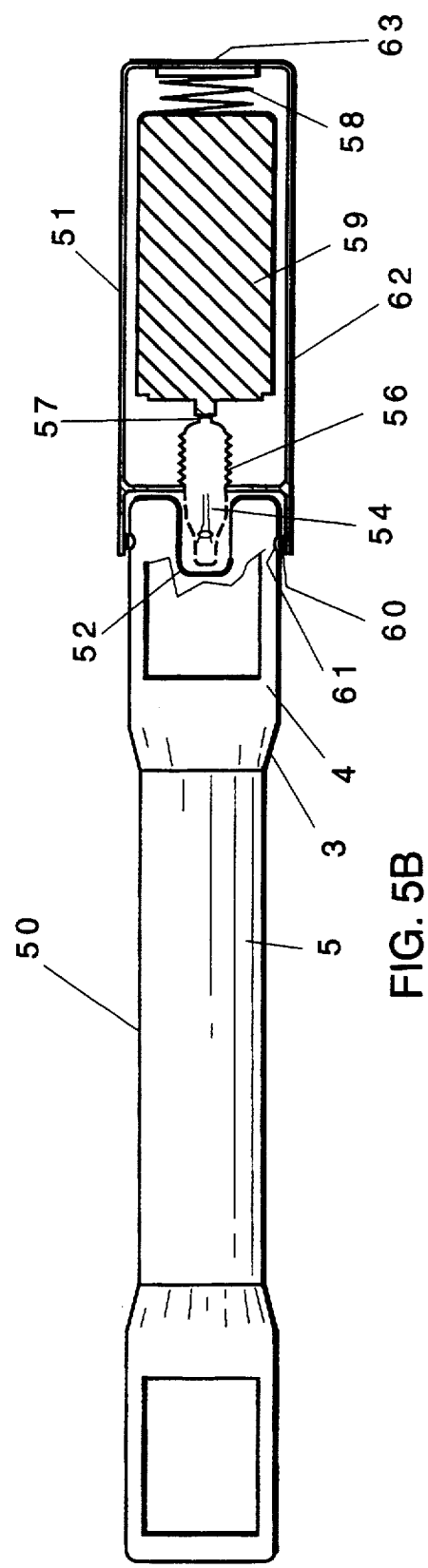
FIG. 5A
FIG. 5B

SUB-SURFACE VISUALIZATION DEVICE

FIELD OF INVENTION

The invention relates to a device for increasing the visualization of body surfaces and sub-surfaces and in particular for the purposes of examining the condition of pre-emergent teeth beneath the gum surface.

BACKGROUND

Common to all young children is the emergence of teeth through the gums which is associated with discomfort and pain. Parents and pediatricians alike are often frustrated in their efforts to determine whether a child's discomfort and irritability is because of "teething" or some other reason. At present there is no simple way to make this determination. The experienced pediatrician may palpate the gums and look for redness but this method is useful only in the advanced stages of emergence of teeth.

There has been a device developed which assists in the examination of the tooth-jaw structure as in U.S. Pat. No. 4,564,355, entitled "Method and Apparatus for the non-invasive examination of the Tooth-Jaw structure of a patient to determine the characteristics of unerupted teeth and to control nutritional intake pursuant thereto" and issued to Harry A. and Mark A. Traiger. This rather elaborate device uses a source of illumination and an opto-detector in conjunction with a linear displacement transducer to provide size, distance and spatial measurements of structures in the jaw. This expensive and complex system is for use in a dental office by trained professionals. A cited benefit of this device is as an alternative to using x-rays, especially in young children. Other devices have been developed for use by the dentist in illuminating and/or increasing visualization in the patient's mouth. For example U.S. Patent No. 4,790,751, entitled "Dental Viewing Apparatus and Method" issued to Richard Reinhardt, and Roca and Gerald Tussing, which is incorporated herein by reference, uses a fiber optic light guide and source with an intensity sufficient for transillumination. The apparatus is incorporated into an instrument to deliver air and water flow as well. This apparatus, like the previous one is only suitable for dental professionals. A number of articles on using fiberoptics for illumination of the oral cavity are referenced in the patent.

Another area pertinent to the present invention is magnifiers. While there are a number of patents issued to inventors of magnifiers, none are expressly for dental applications. Among the patents relating to magnifiers are U.S. Pat. No. 4,483,588 entitled "Magnifier with Reference Line" issued to Emil and Lorraine Dalbo, incorporated herein by reference, and U.S. Pat. No. 4,757,616 entitled "Ruler with Magnifying Cursor" issued to Brian Hills. In both of these patents the magnifier portion is a single cylindrical type lens held very close to the material needing to be magnified.

A refinement of magnifying devices is to provide a source of illumination. Fiber optic light guides have been incorporated into some dental devices as those referenced above. Other approaches are for general purpose magnifiers. For example U.S. Pat. No. 5,168,405 issued to Richard Feinbloom, incorporated herein by reference, illustrates use of a light diffuser comprised of an annular light pipe which is abraded to diffuse light uniformly over a surface being viewed through a lens held over the surface. While illustrative of a method for introduction of additional illumination using a light pipe, an annular ring is not appropriate in the present application.

None of the foregoing devices or methods address the need for an inexpensive, easy-to-use device which enables the lay person to determine whether pre-emergent teeth are pushing through the gums of small children. By taking a simpler approach than is typical in dental applications, the present invention solves a major problem.

SUMMARY OF THE INVENTION

The invention provides a device to assist parents and health care providers in determining whether discomfort of a non-verbal child results from impending emergence of teeth through the gums.

The invention provides a method and apparatus for visualizing the substructure of gums of infants and young children. It comprises a means for pressing against the gums and magnifying the structure below. This may be done using ambient light and/or with the addition of other light. Wings or handles on one or both ends of the magnifier/compression portion of the device facilitate holding the device from outside the mouth and also serve as an alignment aid and deterrent to choking on the device.

One version of the invention involves a clear plastic cylindrical-type linear lens with integral handles for ease of holding by the viewer. The design of the lens and attached handles is such that ambient and/or special directed sources of light may be used to brighten the viewing area.

A lens is pressed against body tissue which serves to vacate the underlying area of blood, further enhancing contrast between bone/teeth structure and flesh.

The present invention may be useful in several applications. In addition to use in infants and young children for determining placement and development of pre-emergent teeth, it would be helpful in older persons with impending gum diseases or deterioration in the root of the tooth. In addition, the device can be used with animals when underlying structures of surface tissues are of interest.

Objects of the present invention are more readily appreciated and understood from the detailed description of the preferred embodiments with the accompanying drawings.

BRIEF DESCRIPTION OF THE DRAWINGS

FIG. 5a and 5b are side and top views with partial cut-aways respectively of a modified version of the apparatus of FIG. 1 such that a source of illumination is incorporated.

DETAILED DESCRIPTION

Figure 1:
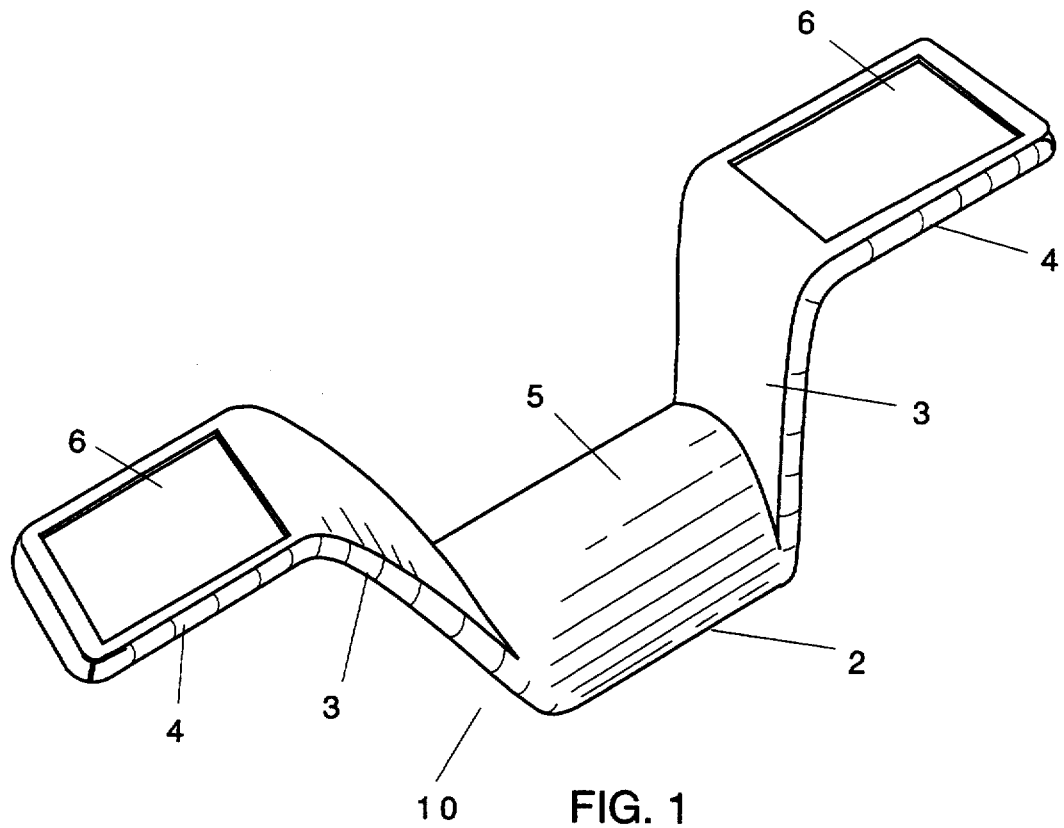
FIG. 1 is a perspective front view of one embodiment of a pre-emergent tooth visualizing apparatus constructed in accordance with the present invention.
Figure 2:
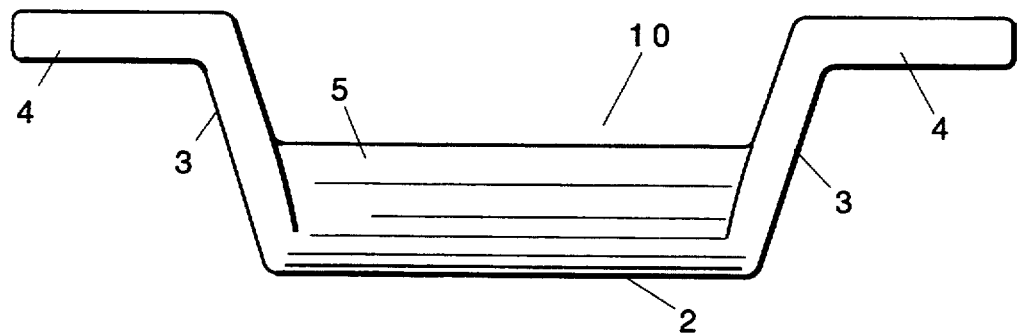
FIG. 2 is side view of the apparatus of FIG. 1, showing relative lengths of various parts.

Shown in FIGS. 1, 2, and 3 is a hand held magnifying device 10 of the present invention. Referring now to FIG. 1, the invention 10 has a magnifier/viewing area 5 opposing a contact area 2; offsetting end connectors 3; and handles 4. The handles have an optional area for providing gripping pads 6. In the present configuration each of these sections is formed as an integral single piece having optical clarity throughout. The magnifying means may be chosen from magnifying lenses, regular geometrical patterns, light filters, and liquid crystals.

Referring now to FIG. 2, a side view, there is more clearly shown the approximate relationship between the sections of device 10. The magnifying section 2, which in the principal application would be placed into the mouth, is on the order of 30-40 mm in length and 10 mm in cross section. The offsetting end connectors 3 provide 10-20 mm of extension from the handles 4 which are outside the mouth. The handles 4 which serve the multiple purposes of orienting the viewing section 5; providing a means for holding the device; and providing a size and shape which is difficult to accidently swallow, are on the order of 15-30 mm in length and 2-10 mm in thickness. In one modification of the present invention (see FIGS. 5a and 5b), the handles 4 and connecting sections 3 also serve to convey light to the viewing area 5.

Figure 3A:
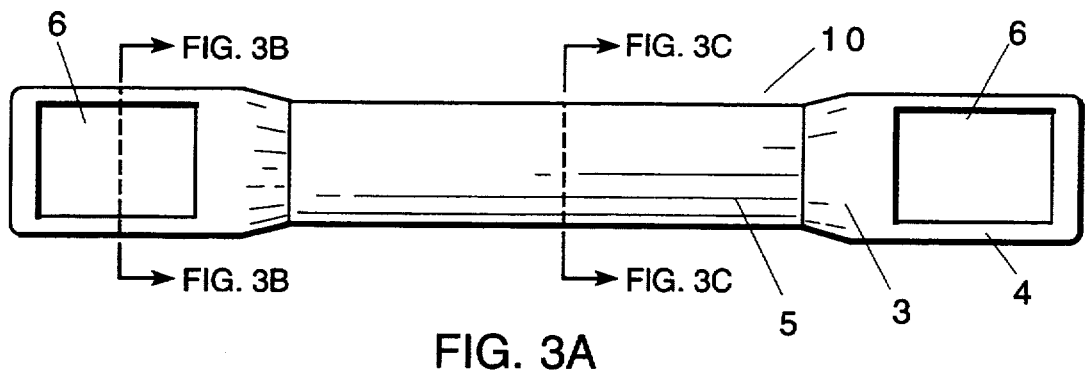
FIG. 3a is top view of the apparatus of FIG. 1.

FIG. 3a, shows a top view of the device 10 as it would normally be viewed when in use. The approximate width of the handles 4 is shown in relationship to the width of the viewing area 5 and connecting section 3. Each section is of similar if not identical width; namely, in the range of 5-15 mm. An area 6 for providing additional grip is also indicated. This could be accomplished in any number of ways: molded into the original product, added to the device after formation (as by affixing grit paper with adhesive for example), and/or by etching, sandblasting or otherwise treating the area.

Figure 3B:
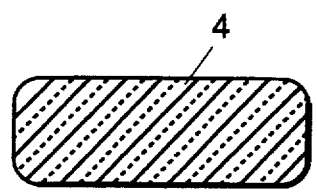
FIGS. 3b and 3c show cross sections of the side pieces/handles and the central magnifying section, cut along lines 3b—3b and 3c—3c of FIG. 3a, respectively.
Figure 3C:
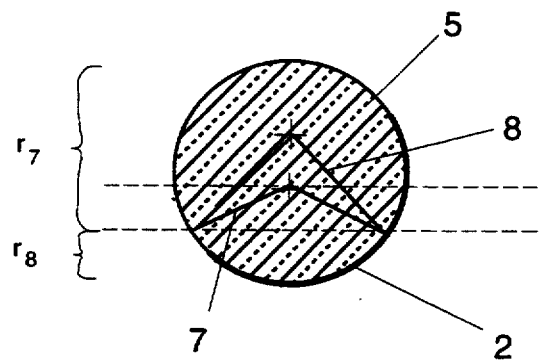

The cross section of the handle taken at line 3b—3b is seen in FIG. 3b. While the shape could be more or less rounded, oval, squared, or irregular, the rectangular shape shown is practical for low cost tooling and production. The cross section of the viewing section taken at line 3c—3c is seen in FIG. 3c. This cross-section prevails throughout the viewing area 5. The 3c—3c cross-section shows two different radii of curvature. The top portion 5 has a substantially uniform curvature defined by r(7). The bottom portion, which is pressed to the surface being viewed, has a curvature defined by r(8) where r(8) is generally greater than r(7), that is, the bottom portion 2 is flatter than the viewing portion 5. In fact, the bottom portion 2 may be flat without compromising performance of the device. A suitable range of curvatures for R7 is 4-15 mm. A suitable range of curvatures for R8 is equal to or greater than 5 mm. The range of curvature for the top portion 5 is determined in part by the diameter of the device in the viewing section which for the reference embodiment ranges from 10-25 mm. The materials for the device 10 may be of glass or optically clear plastics from the family of acrylic, polycarbonate, styrene or such other materials having similar optical and forming properties. Suitable materials for a light pipe include clear and colored glass and polymers. Note that requirement for optical clarity does not preclude using a lightly tinted material. The handle 4 and offset connector 3 do not need to be optically clear or smooth for the embodiment of FIG. 1. In fact, handles 4 can be roughened to provide a better grip surface 6. Alternatively a gripping surface can be cemented to the handle after formation or all but area 6 could be screened during etching or surface treatment.

Figure 4:
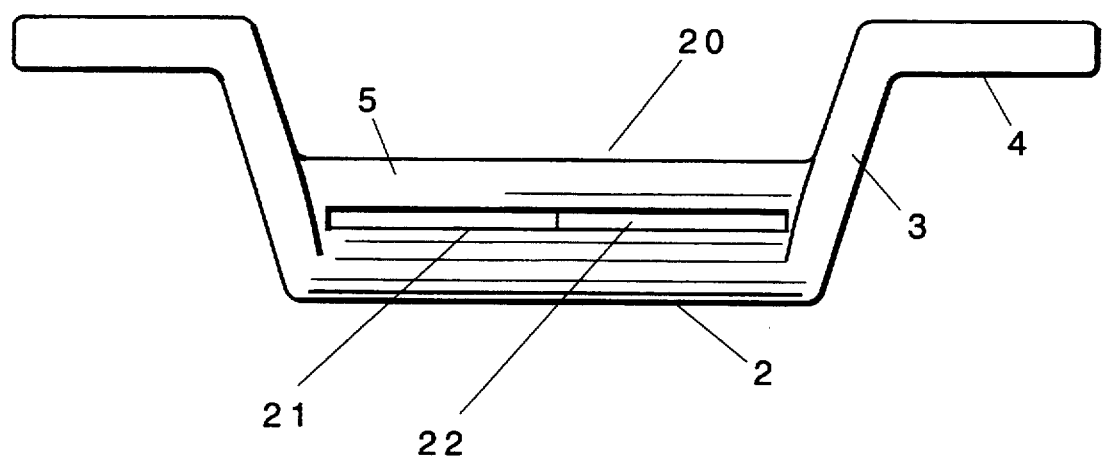
FIG. 4 is a side view of a modified version of the apparatus of FIG. 1 which will accommodate insertion of one or more filters to change contrast in the surface viewed.

Referring now to FIG. 4, a variation of the device of FIGS. 1-3 is shown. This device 20 is distinguished by having one or more slots (21 and 22) in the side of the device interposed between the viewing area 5 and the lower contact surface 2. The purpose of such slots which project across the entire width of the center section is to provide for a change of color or to view the tissue simultaneously with two different colors in the optical path for greater discrimination between different tissues viewed (as between flesh, bone and teeth).

FIGS. 5a and 5b illustrate another variation on the basic device. In this variation an external light source is provided to brighten the viewing area. Referring now to FIG. 5a, a side view of device 50 and partial cutaway of housing 51, at least one of the handles 4 of device 50 is hollowed out to form a cavity 52 into which an electric lamp 54 is inserted. Said lamp is supported in a housing 51 which contains a lamp mount, battery and connecting apparatus. The housing 51 also is shaped so as to fit around the end of the handle 4 and form a mechanical connection thereto in part through use of detentes 53. The handle 4 and offsetting connector 3 serve as a light pipe to convey light to the viewing 5 and contact 2 areas. Effective conveyance is dependent upon having a high optical transmission material (such as glass and some plastics like acrylic) and a gradual change in slope at the juncture of the handle and the connecting arm 55. If the curvature is much sharper than shown there will be loss of light out the sides of the device.

Referring now to FIG. 5b, a top view of device 50 with a cut-away view of housing 51, points of attachment 60 and 61 of housing 51 to device 50 are indicated. Details of the light source and its housing 51 are seen. Lamp 54 screws or twists into a socket 56 which has an insulted end button 57 which makes contact with one end of a battery 59. The other end of the battery is contacted via a spring 58 which is electrically connected to a wire or strip 62 which is connected to the lamp socket wall, thereby completing the circuit. An alternative would be to provide a switch and/or integrate a switch into the design whereby pressing the end of the housing 63 pushes against a spring on the opposite end (not shown) of the battery (which keeps the battery away from contact button 57) to complete the circuit. Hole 52 in the handle is fashioned to follow the contour of electrical lamp 54 used. The lips of housing 51 which fit over the handle serve not only as a means for mechanical attachment but are also designed so that light from the lamp is directed back into the handle.

Figure 6:
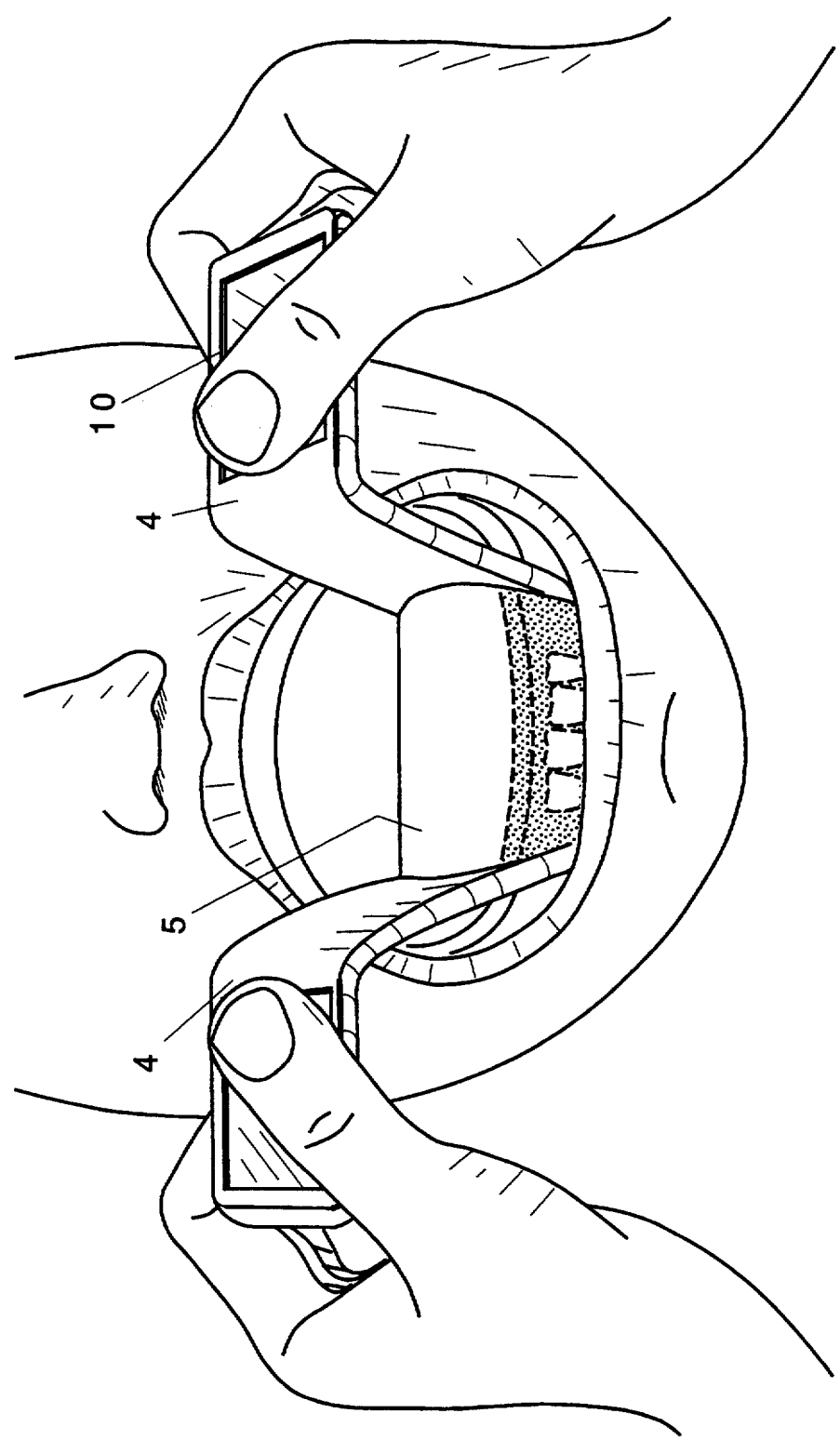
FIG. 6 illustrates one method for using the apparatus of FIG. 1 to visualize pre-emergent teeth.

Referring now to FIG. 6, a method for application of the device is illustrated. The device 10 is held in both hands by the two handles 4 and the viewing/magnifying section 5 is placed into the mouth and pressed against the gums to expose the outline of underlying teeth. The surface of the device is compressible against the flexible environment of the gums. Other configurations of the visualization device would be obvious given a particular material or application in the mouth or on other body surfaces.

What is claimed is:

1. A sub-surface visualization device for indicating the presence of unerupted teeth in the gums of a patient, comprising:
- a transparent member having a first end, a second end, and at least a first curvilinear surface extending therebetween and defining a longitudinal axis;
- a first offsetting connecting member extending upwardly from said first end and extending away from said longitudinal axis, said first offsetting connecting member terminating in a first handle member, said first handle member including hand gripping means;
- a second offsetting connecting member extending upwardly from said second end and extending away from said longitudinal axis, said second offsetting connecting member terminating in a second handle member, said second handle member including hand gripping means;
- said first and second handle members being integral with said transparent member and spaced from said longitudinal axis; and
- magnification means mounted on said transparent member, whereby said transparent member is adapted to be pressed against the gums of a patient and said magnification means indicates the presence of unerupted teeth therein.

* * * * *